(12) United States Patent
Gupta et al.

(10) Patent No.: US 11,654,271 B2
(45) Date of Patent: May 23, 2023

(54) VASCULAR ACCESS WITH RETROGRADE AND ANTEGRADE DELIVERY MODES

(71) Applicant: PHVC Scientific LLC, Zephyrhills, FL (US)

(72) Inventors: Sunil Gupta, Wesley Chapel, FL (US); Chetan Khamare, Lutz, FL (US); Ketul Chauhan, Wesley Chapel, FL (US); Vikas Reddy Soma, Tampa, FL (US); Derek O'Hara, Tampa, FL (US)

(73) Assignee: PHVC Scientific LLC, Zephyrhills, FL (US)

( * ) Notice: Subject to any disclaimer, the term of this patent is extended or adjusted under 35 U.S.C. 154(b) by 210 days.

(21) Appl. No.: 16/838,168

(22) Filed: Apr. 2, 2020

(65) Prior Publication Data

US 2020/0316357 A1  Oct. 8, 2020

Related U.S. Application Data

(60) Provisional application No. 62/829,157, filed on Apr. 4, 2019.

(51) Int. Cl.
*A61M 39/02* (2006.01)
*A61M 25/10* (2013.01)
*A61M 25/09* (2006.01)

(52) U.S. Cl.
CPC .. *A61M 39/0247* (2013.01); *A61M 25/09041* (2013.01); *A61M 25/10185* (2013.11); *A61M 2039/0258* (2013.01)

(58) Field of Classification Search
CPC .... A61M 2039/0258; A61M 25/10185; A61M 25/09041; A61M 39/0247
See application file for complete search history.

(56) References Cited

U.S. PATENT DOCUMENTS

| | | | | |
|---|---|---|---|---|
| 7,918,859 | B2 * | 4/2011 | Katoh | A61B 17/320725 606/113 |
| 11,147,573 | B2 * | 10/2021 | Nakagawa | A61M 25/00 |
| 2016/0106499 | A1 * | 4/2016 | Ogata | A61B 18/1492 606/29 |
| 2017/0007292 | A1 * | 1/2017 | Conn | A61B 6/12 |

* cited by examiner

*Primary Examiner* — Dung T Ulsh
(74) *Attorney, Agent, or Firm* — Fenwick & West LLP

(57) ABSTRACT

Disclosed is a system for vascular access, where the system allows for transitions between retrograde and antegrade access without generation of multiple access sites and without inducing extensive vascular damage. In embodiments, the system can include a vascular access portion including a body with a first lumen for preferentially providing access in a retrograde direction into a vessel, and a second lumen for preferentially providing access in an antegrade direction into the vessel. The body can be transitioned (e.g., by way of expansion, contraction, or other deformation mode) between a retrograde delivery mode and an antegrade delivery mode.

8 Claims, 10 Drawing Sheets

300

Receive and transmit a first guidewire in a retrograde direction 310

Transition from first mode to second mode 320

Receive and transmit a second guidewire (or the first guidewire) in an antegrade direction 330

Transition out of second mode 340

Remove body while second guidewire is in position for antegrade delivery 350

FIG. 3

VASCULAR ACCESS WITH RETROGRADE AND ANTEGRADE DELIVERY MODES

CROSS REFERENCE TO RELATED APPLICATIONS

This application claims the benefit of U.S. Provisional Application Ser. No. 62/829,157 filed 4, Apr. 2019, which is incorporated in its entirety herein by this reference.

BACKGROUND

This disclosure relates generally to vascular access devices and surgical methods, and more specifically to devices and methods that allow transitions between retrograde and antegrade vascular access modes, by a medical device, through a single access site.

Many medical procedures begin with accessing vasculature through an access site and routing subsequent medical devices through the access site. In more detail, many procedures begin with accessing a superficial femoral artery (SFA) through a common femoral artery (CFA) access site, and then passing subsequent medical devices in a retrograde direction through the SFA. In one such method for introducing a catheter into the SFA, a vascular access needle is inserted into the CFA, and a guidewire is inserted through the vascular access needle into the CFA and manipulated to the SFA. The vascular access needle is then removed, and an introducer is routed about the guidewire into the CFA and SFA. Finally, the guidewire is removed and a catheter or other medical device is routed through the introducer to perform one or more portions of the medical procedure. If the access procedure and/or physiological obstructions (e.g., occlusions) along the intended path of medical device transmission prohibit retrograde delivery, current methods require generation of a second access site (e.g., at a contralateral location), which can create significant complications that are attributed to routing medical devices through vasculature along a longer and less direct path to the treatment site. Repeated puncturing at or near a particular access site is also not practical and/or not advised due to damage of the vasculature with each instance of access. In particular, if initial attempts at access are not successful, practitioners typically apply pressure to the access site for a period of time to stop the bleeding, with patients returning to re-initiate treatment after a long period of time (e.g., 30 days) while being on anticoagulants. The ability to transition between retrograde and antegrade delivery modes, with a single device and single access site, would be invaluable in allowing procedures to continue if initial attempts at access along a first direction are not successful.

SUMMARY

Disclosed is a system for vascular access, where the system facilitates performance of peripheral vascular intervention procedures, and allows for transitions between retrograde and antegrade access without generation of multiple access sites and without inducing extensive vascular damage. In embodiments, the system can include: a vascular access portion including a body with a first lumen for allowing a first guidewire to be transmitted in a retrograde direction into a vessel, and a second lumen for allowing the first guidewire or a second guidewire to be transmitted in an antegrade direction into the vessel. The body can be transitioned (e.g., by way of expansion, contraction, or other deformation mode) between a first mode for preferentially allowing retrograde access of the first guidewire, through the first lumen, to the vessel, and a second mode for preferentially allowing antegrade access of the first guidewire or a second guidewire, through the second lumen, to the vessel.

The system can enable a method for accessing a vessel in a first direction and transitioning access from the first direction to a second direction opposed to the first direction, without generation of multiple access sites and without inducing extensive vascular damage. In embodiments, the method can include: providing a first pathway, through a first lumen of a body, into a vessel in a first direction (e.g., a retrograde direction); and providing a second pathway, through a second lumen of the body, along a second direction (e.g., an antegrade direction) into the vessel. In some embodiments, the method can include transitioning the body between a first mode for preferentially allowing retrograde access through the first lumen to the vessel, and a second mode for preferentially allowing antegrade access through the second lumen to the vessel. In relation to vascular access, embodiments of the system and/or method thus allow access by one or more guidewires, introducers, and/or medical devices (e.g., for introducing contrast agents, surgical instruments, catheters, imaging devices, etc.), to a vessel in multiple directions, without requiring repeated insertion of a vascular access needle and/or requiring multiple punctures at contralateral peripheral access sites.

BRIEF DESCRIPTION OF THE DRAWINGS

FIG. 3 is a block diagram of a method for vascular access, in accordance with one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

1. System for Vascular Access

Figure 1:
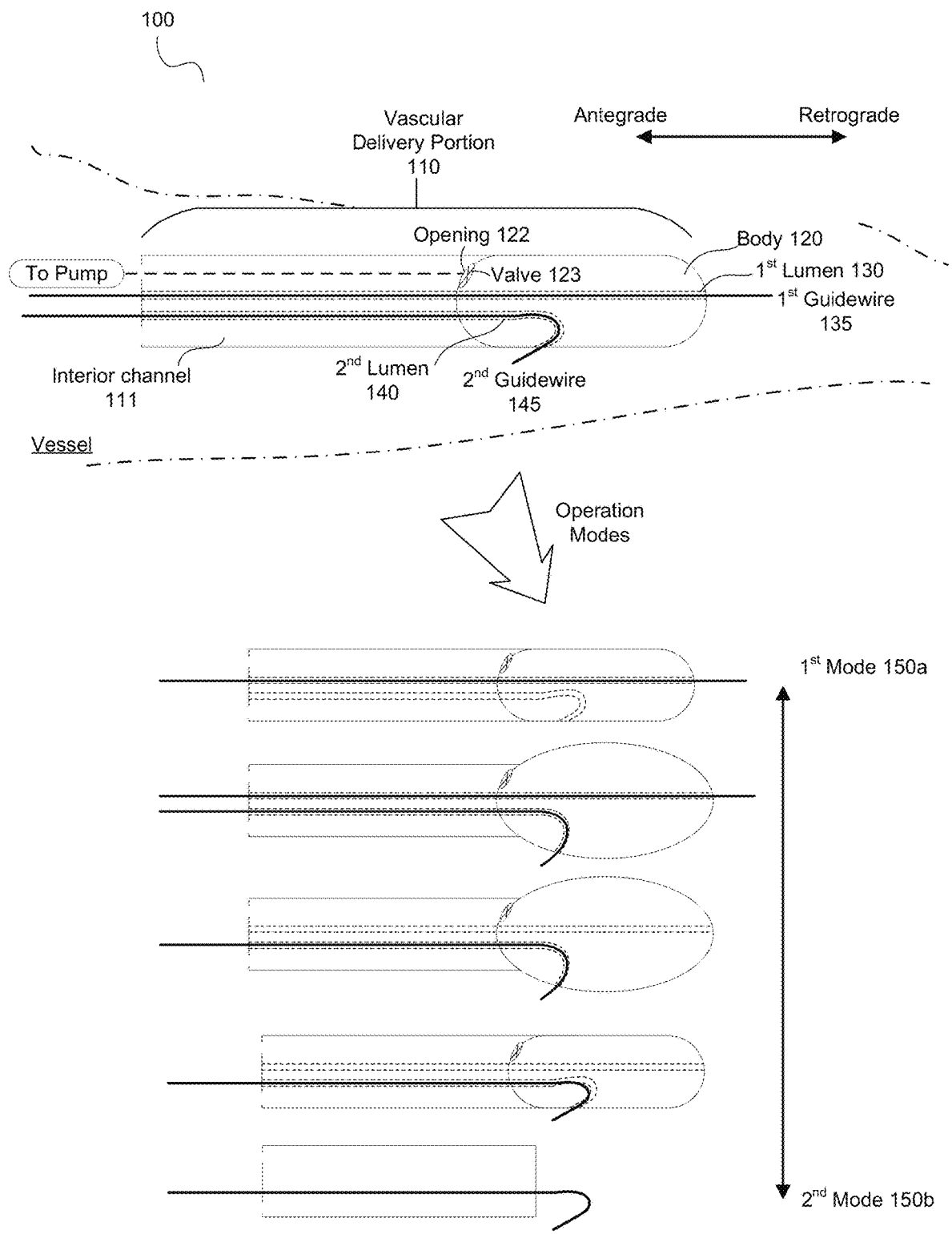
FIG. 1 is a schematic of a system for vascular access, in accordance with one or more embodiments.

FIG. 1 is a schematic of a system 100 for vascular access, in accordance with one or more embodiments. The system 100 shown in FIG. 1 includes a vascular delivery portion 110 including a body 120 with a first lumen 130 for allowing a first guidewire 135 to be transmitted in a retrograde direction into a vessel, and a second lumen 140 for allowing the first guidewire or a second guidewire 145 to be transmitted in an antegrade direction into the vessel. The body 120 can be transitioned (e.g., by way of expansion, contraction, or other deformation mode) between a first mode 150*a* for preferentially allowing retrograde access of the first guidewire, through the first lumen, to the vessel, and a second mode 150*b* for preferentially allowing antegrade access of the first guidewire or a second guidewire, through the second lumen, to the vessel, in a manner that does not require a second puncture site or repeated puncture at a first puncture site. The system 100 thus functions to allow access by one or more guidewires, introducers, and/or medical devices (e.g., for introducing contrast agents, surgical instruments, catheters, imaging devices, etc.), to a vessel in multiple directions, without requiring repeated insertion of a vascular access needle and/or requiring multiple punctures at contralateral peripheral access sites.

Embodiments of the system 100 can implement one or more embodiments of the method described in section 2 below, or can alternatively implement other methods.

1.1 System—Vascular Access Portion and Body

As shown in FIG. 1, the system 100 includes a vascular delivery portion 110, which functions to transport the body 120 of the vascular delivery portion 110 throughout vasculature of a patient and toward a desired physiological site associated with subsequent treatment or examination. The vascular delivery portion 110 can be a dilating element (e.g., dilator) that functions to dilate the target vessel being accessed (or a vessel portion along a vascular pathway to the target vessel) in relation to a performed procedure. The vascular delivery portion 110 can additionally or alternatively be an introducer through which other medical devices or materials can be passed, directly to the target vessel site. The vascular delivery portion 110 can be configured to pass through a vascular access device (e.g., vascular access needle that punctures vasculature of a patient to provide an initial access site) in order to enable subsequent steps of a procedure to be performed.

In morphology, the vascular delivery portion 110 is an elongated member that includes an interior channel 111 for allowing passage of devices, objects, or materials through the vascular delivery portion 110 and the body 120, and toward the desired physiological site of the patient. In relation to providing pathways to different lumens of the body 120 described below, the vascular delivery portion 110 can include more than one interior channel, where multiple interior channels can define pathways to different portions of the body 120. The vascular delivery portion shown in FIG. 1 is circular in cross section taken transverse to a longitudinal axis of the vascular delivery portion 110, and the cross section of the vascular delivery portion 110 is substantially uniform along the length of the vascular delivery portion 110; however, in alternative embodiments, the vascular delivery portion can have another cross-sectional morphology and/or be non-uniform in cross section along its length.

In embodiments, the morphology of the vascular delivery portion 110 can have one or more of: an outer diameter (or width) from 0.1 mm-5 mm, an inner diameter (or width) from 0.05-4.8 mm, a wall thickness from 0.02-0.4 mm, and a length from 5-100 mm. The morphology of the vascular delivery portion 110 can alternatively be configured as a needle with a gauge from 7-34 gauge. The vascular delivery portion 110 can, however, have any other suitable morphology.

The vascular delivery portion 110 can be composed of a biocompatible material, and in an example, can be composed of stainless steel. However, in other embodiments, the vascular delivery portion 110 can be composed of or include regions composed of other biocompatible metallic materials (e.g., cobalt chrome, nickel, nitinol, etc.). In other embodiments, the vascular delivery portion 110 can additionally or alternatively be composed of or include regions composed of other biocompatible materials (e.g., polymers, ceramics, etc.).

The vascular delivery portion 110 can include rigid portions and/or can include deformable portions. In relation to mechanical properties, the vascular delivery portion 110 is configured to be robust against failure (e.g., fracture, fatigue) under relevant sheer, bending, compressive, and tensile stresses encountered during use and insertion into a patient, vessel, or other object. Additionally or alternatively, in relation to mechanical properties, the vascular delivery portion can be configured to operate appropriately under physiological constraints (e.g., diameter of vessel, tortuosity of vessel, etc.). As such, the vascular delivery portion 110 can have a shear strength, a compressive strength, a tensile strength, an elastic modulus, a hardness, a derivative of the above mechanical properties and/or other properties that enable robustness in use, in association with feature dimensions and operation modes described below. In specific examples, the vascular delivery portion 110 can have a shear strength greater than 10 MPa, a compressive strength greater than 10 MPa, a tensile strength greater than 10 MPa, an elastic modulus greater than 10 MPa, and a Brinell hardness greater than 10. However, the vascular delivery portion 110 can alternatively have other properties (e.g., thermal properties, electrical properties, etc.) associated with different applications of use.

The vascular delivery portion 110 can include elements integrated with the elongated member (e.g., along interior channel 111) that facilitate steering of the vascular delivery portion 110 once inserted at the access site. For instance, the vascular delivery portion 110 can include shape memory material regions (or can be composed of shape memory materials) that can be manipulated by heat, electric currents, and/or other stimuli in order to induce morphological changes that adjust the shape of desired portions of the vascular delivery portion 110 during use. In another example, the vascular delivery portion 110 can include elements (e.g., one or more regions of material) that can be steered by actuation and/or by applied external forces (e.g., magnetic forces) to guide movement of desired portions of the vascular delivery portion 110 once inserted at the access site. In one such example, a portion of the vascular delivery portion 110 can be composed of a material that responds to applied magnetic forces, thereby enabling applications involving magnetic steering of the vascular delivery portion and associated elements to a desired treatment site.

Additionally or alternatively, in another example, the vascular delivery portion 110 can include elements (e.g., one or more regions of material) that are optically detectable using remote imaging systems, thereby enabling image-based guidance of the vascular delivery portion and associated elements to a desired treatment site.

1.1.1 Vascular Delivery Portion—Body

The body 120 of the vascular delivery portion 110 functions to support one or more lumens (described below) that provide pathways for guidewires and/or other materials to enter the target vessel in retrograde and/or antegrade directions. In embodiments, the body 120 is also structurally transitionable between different forms associated with operation modes for retrograde and antegrade access, as described in further detail below. The body 120, as shown in FIG. 1, is coupled to a distal end of the vascular delivery portion 110 (e.g., dilator, introducer); however, the body 120 can alternatively be coupled to another suitable portion of the vascular delivery portion 110. In embodiments, after guidewire placement within a vessel, the body 120 can be uncoupled from or otherwise removed from the vascular delivery portion 110 (e.g., through an interior portion of the vascular delivery portion 110), such that other elements (e.g., introducers, catheters, etc.) can be routed about the guidewire(s) for subsequent phases of treatment.

In morphology, the body 120 has a length and distal end with a rounded tip, in order to facilitate movement of the body 120 within a vessel without inducing extensive damage to the vessel. The body 120, as shown in FIG. 1, is substantially straight (e.g., has a predominating longitudinal axis); however, in other embodiments, the body 120 can have curved portions (e.g., regions that deviate from a linear axis). The body 120 shown in FIG. 1 is circular in a cross section taken transverse to the longitudinal axis; however, in other embodiments, the body 120 can have another cross-sectional morphology taken across a suitable axis.

In relation to the operation modes for retrograde and antegrade access described in Section 1.3 below, the body 120 can be configured to transition between a baseline configuration and at least one other configuration (e.g., by way of expansion, contraction, or other deformation mode). As shown in FIG. 1, the body 120 is configured as a balloon that can be expanded from a baseline configuration to an expanded configuration, in order to promote passage of a guidewire along a desired pathway (e.g., retrograde direction, antegrade direction) through a lumen of the body 120. As such, as shown in FIG. 1, the body 120 can include an opening 122 (e.g., with a valve 123) that provides access to a pumping element (e.g., syringe) for transitioning the body 120 between the baseline configuration and the expanded configuration. In this embodiment, the body 120 can thus have an interior cavity that can be expanded and/or contracted with application of positive/negative pressure. However, in other embodiments, the body 120 can be configured to deform in any other suitable manner (e.g., based upon chemical reactions within the body 120, based upon thermal expansion and contraction, based on mechanical deformation, etc.). In still other embodiments, the body 120 may not be configured to deform or undergo morphological changes during use.

The morphology of the body 120 can have one or more of: an outer diameter (or width) from 0.1 mm-10 mm, an inner diameter (or width) from 0.05-9.6 mm, a wall thickness from 0.01-0.8 mm, and a length from 5-50 mm, in baseline and/or expanded configurations.

In embodiments, the body 120 is composed of a flexible and/or biocompatible polymer (e.g., nylon, Pebax, polyethylene terephthalate, polyurethane, etc.) that can repeatedly undergo transitions between a baseline and expanded configuration; however, in other embodiments, the body 120 can be composed of another polymer material or non-polymer material.

In relation to mechanical properties, the body 120 is configured to be robust against failure (e.g., bursting, leaking) under relevant sheer, compressive, and tensile stresses encountered during use (e.g., due to flow and/or pressures experienced within a vessel, due to vessel morphology, due to vessel tortuosity, etc.). As such, the body 120 can have a shear strength, a compressive strength, a tensile strength, an elastic modulus, a derivative of the above mechanical properties and/or other properties that enable robustness in use, in association with feature dimensions and operation modes described below. In specific examples, the body 120 can have a shear strength greater than 10 MPa, a compressive strength greater than 10 MPa, a tensile strength greater than 10 MPa, and an elastic modulus greater than 10 MPa. However, the body 120 can alternatively have other properties (e.g., thermal properties, electrical properties, etc.) associated with different applications of use, in relation to dilation and/or passing of other devices or materials in retrograde and antegrade directions.

1.2 System—Lumens and Guidewires

As shown in FIG. 1, the body 120 includes a first lumen 130 for allowing a first guidewire 135 to be transmitted in a retrograde direction into a vessel, and a second lumen 140 for allowing the first guidewire or a second guidewire 145 to be transmitted in an antegrade direction into the vessel. The first lumen 130 thus functions to preferentially provide access or promote transmission of a guidewire in a first direction (e.g., retrograde direction) once the body 120 is positioned within a target vessel, and the second lumen 140 functions to preferentially provide access or preferentially promote transmission of a guidewire in a second direction (e.g., antegrade direction) once the body 120 is positioned within a target vessel.

The first lumen 130, as shown in FIG. 1, is a channel that extends through the body 120 and defines a pathway that allows for guidewire transmission toward a first direction. The first lumen 130 can be defined through a central interior portion of the body 120 (e.g., within a cavity of the body 120), or can be integrated with an interior wall of the body 120. The first lumen 130 can have a first proximal end region that is in communication with an interior channel of the vascular delivery portion 110, and a second distal end region that allows passage of the first guidewire 135 in the first direction. In the embodiment shown in FIG. 1, the first lumen 130 is substantially straight (e.g., defines a linear pathway) and passes along or parallel to a longitudinal axis of the vascular delivery portion 110 and body 120; however, in other embodiments, the first lumen 130 can define another linear or non-linear pathway for guidewire transmission. The cross section of the first lumen 130 (e.g., cross section taken across a plane transverse to the longitudinal axis) can be circular or can be a non-circular shape. In examples, the diameter or width of the cross section of the first lumen 130 can be from 0.02-10 mm for guidewire transmission; however, in other embodiments, the diameter or width of the cross section of the first lumen 130 can have other dimensions.

Similar to the first lumen 130, the second lumen 140 is a channel that extends through the body 120 and defines a pathway that allows for guidewire transmission toward a second direction. The second lumen 140 can be integrated with an interior wall of the body 120 or can be defined in another manner through an interior portion of the body 120 (e.g., within a cavity of the body 120). The second lumen 140 can have a first proximal end region that is in communication with an interior channel of the vascular delivery portion 110, an intermediate region coupled to the proximal end region, and a second distal end region that allows passage of the second guidewire 145 in the second direction. In the embodiment shown in FIG. 1, the second lumen 140 passes into the body and deviates toward the second direction (e.g., antegrade direction), thereby opening at a side of the body 120 between proximal and distal ends of the body 120; however, in other embodiments, the second lumen 140 can define another pathway for guidewire transmission. The cross section of the first lumen 130 can be circular or can be a non-circular shape. In examples, the diameter or width of the cross section of the second lumen 140 can be from 0.02-10 mm for guidewire transmission; however, in other embodiments, the diameter or width of the cross section of the first lumen 130 can have other dimensions.

The first lumen 130 and the second lumen 140 can be isolated from each other, such that either lumen cannot be accessed through the other lumen (e.g., an object or material cannot pass from one lumen to the other). However, the first lumen 130 can alternatively be coupled to the second lumen 140 in a manner where an object can pass between the first lumen 130 and the second lumen 140. Furthermore, embodiments of the system can omit a second lumen, or can have more than two lumens.

The first guidewire 135 and/or the second guidewire 145 function to pass in retrograde and/or antegrade directions within the vessel, and to be used as a guide to route medical devices (e.g., catheters) within vasculature of the patient to perform a subsequent procedure. In composition, the guidewire(s) can be composed of one or more materials, where a first material is used to provide desired mechanical properties and/or enable steering, and a second material is used to provide surface characteristics in relation to biocompatibility, low friction, hydrophilicity, anti-thrombogenesis, hydrophobicity, and/or other design constraints. In embodiments, core portions of the guidewire(s) can be composed of one or more of: gold, nitinol, platinum, stainless steel, nickel, titanium, and tungsten. In embodiments, surface portions of the guidewire(s) can be composed of one or more of: polytetrafluoroethylene (PTFE), silicone, heparin, a hydrophobic material, and/or a hydrophilic material.

In relation to the morphologies of corresponding lumens, the guidewires can be substantially straight, or can include curved or non-straight regions. In examples, the first guidewire 135 can be substantially straight in order to pass through the body 120 in a retrograde direction, and the second guidewire 145 can be curved at a distal region in order to pass through the body 120 in an antegrade direction. In more detail, any of the guidewire(s) can have one or more of: a tip orientation that deviates from a straight path, can have a suitable degree of coaxial alignment, can have an Amplatz left-shaped portion, can have an Amplatz right-shaped portion, can have an extra support portion, can have an extra backup portion, can have a Hockey stick-shaped portion, can have a primary and/or secondary curve with suitable curve lengths, and can have any other suitable regional morphology based on application of use.

The guidewire(s) shown in FIG. 1 are circular in cross section (e.g., a cross section transverse to a longitudinal axis); however, other embodiments of the guidewire(s) can have another morphology. In examples, the diameter or width of the cross section of the guidewire(s) can be from 0.02-10 mm.

1.3 System—Operation Modes

As noted briefly above, the body 120 can be transitioned (e.g., by way of expansion, contraction, or other deformation mode) between a first mode 150a for preferentially allowing retrograde access of the first guidewire, through the first lumen, to the vessel, and a second mode 150b for preferentially allowing antegrade access of the first guidewire or a second guidewire, through the second lumen, to the vessel. As such, the vascular delivery portion 110 is configured to transition between a retrograde delivery mode (i.e., first mode 150a) and an antegrade delivery mode (i.e., second mode 150b), wherein in the retrograde delivery mode, the body preferentially promotes transmission of the first guidewire into the first lumen in the retrograde direction, and wherein in the antegrade delivery mode, the body preferentially promotes transmission of at least one of the first guidewire and a second guidewire into the second lumen in the antegrade direction.

As shown in FIG. 1, the first mode 150a is a baseline mode that preferentially allows the first guidewire 135 to pass through the first lumen 130 of the body in a retrograde direction, where the baseline mode is a deflated configuration (or a configuration of the body that is less than fully expanded). In the first mode 150a, the first guidewire 135 can pass through the interior channel 111 directly into the first lumen 130 of the body 120, to pass into the target vessel in a retrograde direction.

As shown in FIG. 1, the second mode 150b is an expanded mode that preferentially allows a second guidewire 145 (or the first guidewire 135) to pass through the second lumen 140 of the body to pass into the target vessel in a retrograde direction, where transitioning between the first mode 150a and the second mode 150b occurs by way of applying positive pressure within the body 120 through opening 122. In the second mode 150a, the second guidewire 145 (or first guidewire 135) can pass through the interior channel 111 directly into the second lumen 140 of the body, which has been deformed by expansion to allow the guidewire to preferentially pass into the second lumen 140 and to pass into the target vessel in an antegrade direction.

While pressure-associated expansion and deflation are described above with respect to transitioning between the first mode 150a and the second mode 150b, other embodiments of the system 100 can enable other mechanisms for transitions between modes. For instance, transitions can be governed by one or more of: thermal stimuli (e.g., in embodiments where one or more portions of the body 120 include shape memory materials or materials deformed under thermal stimuli), electrical stimuli (e.g., in embodiments where one or more portions of the body 120 include shape memory materials or materials deformed under electrical stimuli), magnetic stimuli (e.g., in embodiments where one or more portions of the body 120 include metallic materials), and any other suitable stimuli.

1.4 System—Specific Example

Figure 2A:
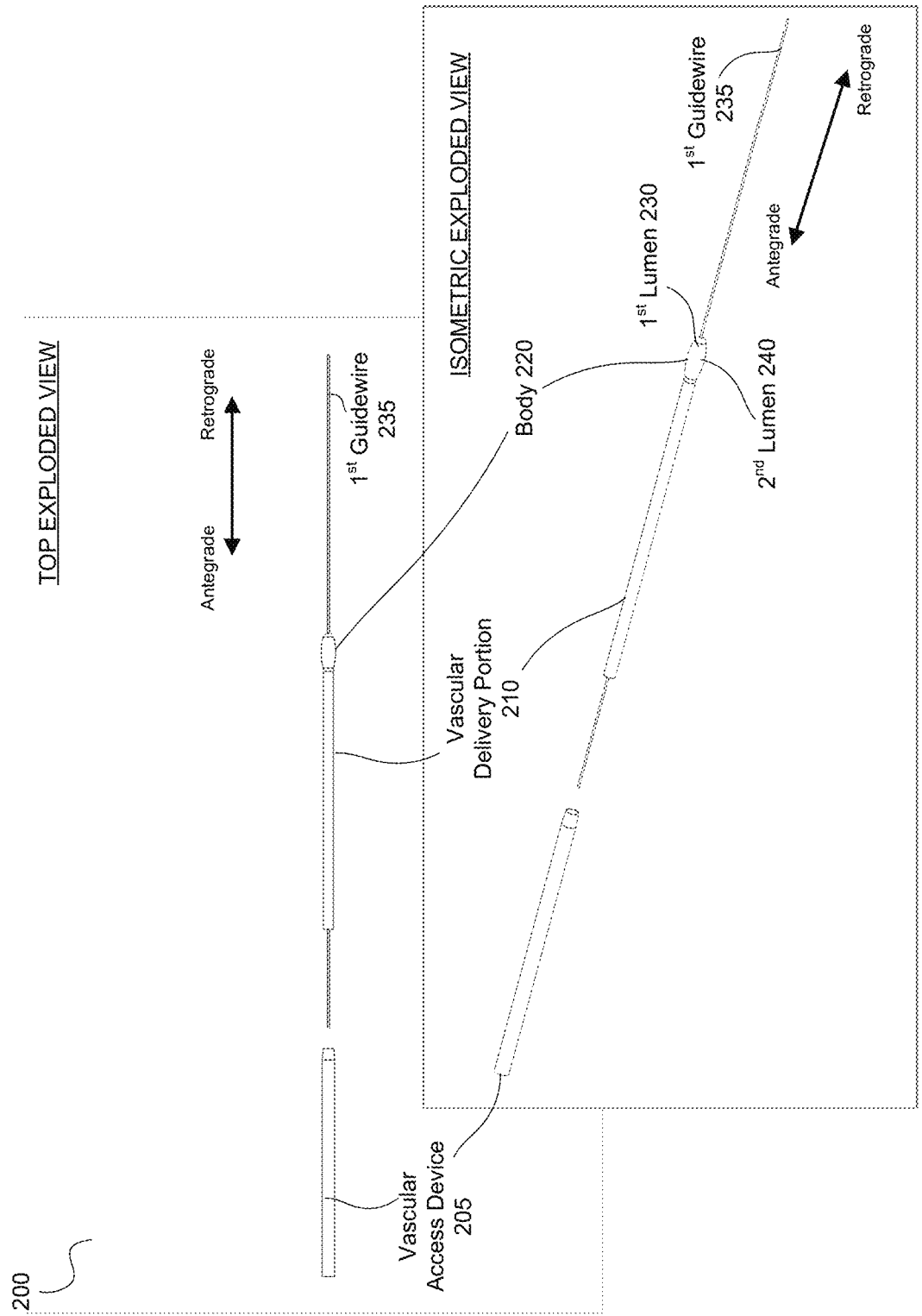
FIG. 2A is an exploded view of an embodiment of the system shown in FIG. 1.

FIG. 2A is an exploded view of an embodiment of the system shown in FIG. 1. The system 200 shown in FIG. 2A includes a vascular access device 205 (e.g., vascular access needle) through which vascular delivery portion 210 is configured to pass in order to access a target vessel for performance of subsequent steps of a procedure. The vascular delivery portion 210 shown in FIG. 2A is a dilator; however, alternative embodiments where the vascular delivery portion is an introducer are described further in Section 1.5 below. The distal end of the vascular delivery portion 210 includes a body 220 configured as a balloon with a first lumen 230 and a second lumen 240 within the interior of the balloon. The first guidewire 235 shown in FIG. 2A is in a configuration where it passes through an interior channel of the vascular delivery portion 210 and through the first lumen 230 for delivery into the target vessel in a retrograde direction.

Figure 2B:
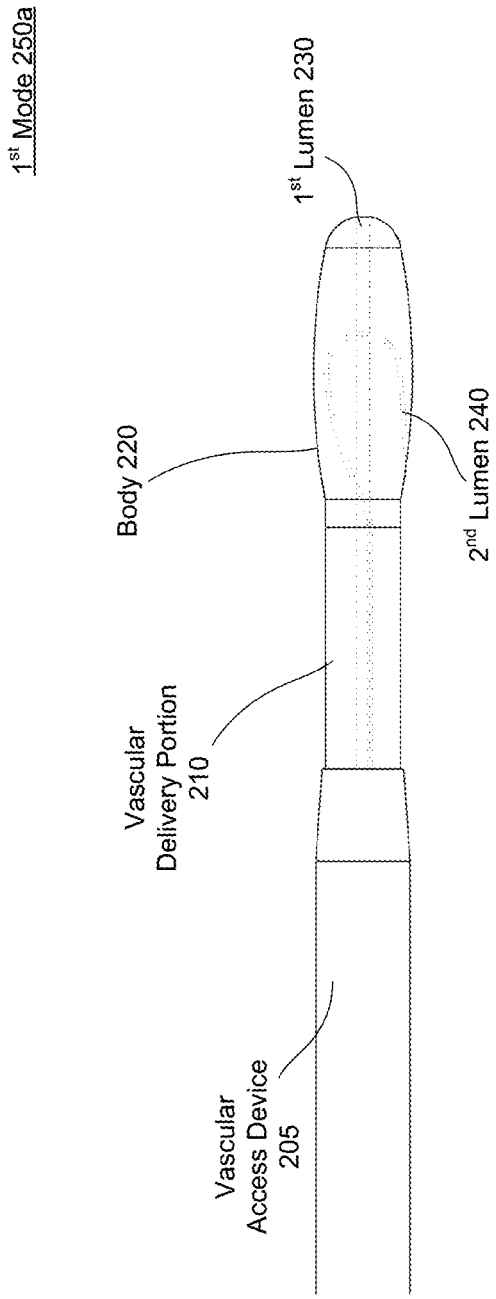
FIG. 2B is a schematic of a first phase of use of an embodiment of the system shown in FIG. 2A.

FIG. 2B is a schematic of a first phase of use of an embodiment of the system 200 shown in FIG. 2A. FIG. 2B is a close-up view of the distal portion of the vascular delivery portion 210 and the body 220 in a first mode 250a of use. In more detail, the first mode 250a is a baseline configuration of the system 200, where the body 220 is in a non-expanded mode. In the first mode 250a, the vascular delivery portion 210, with the body 220 non-expanded, is delivered into a target vessel, and configured to allow a first guidewire 235 to pass through the first lumen 230 of the body 220 in a retrograde direction.

Figure 2C:
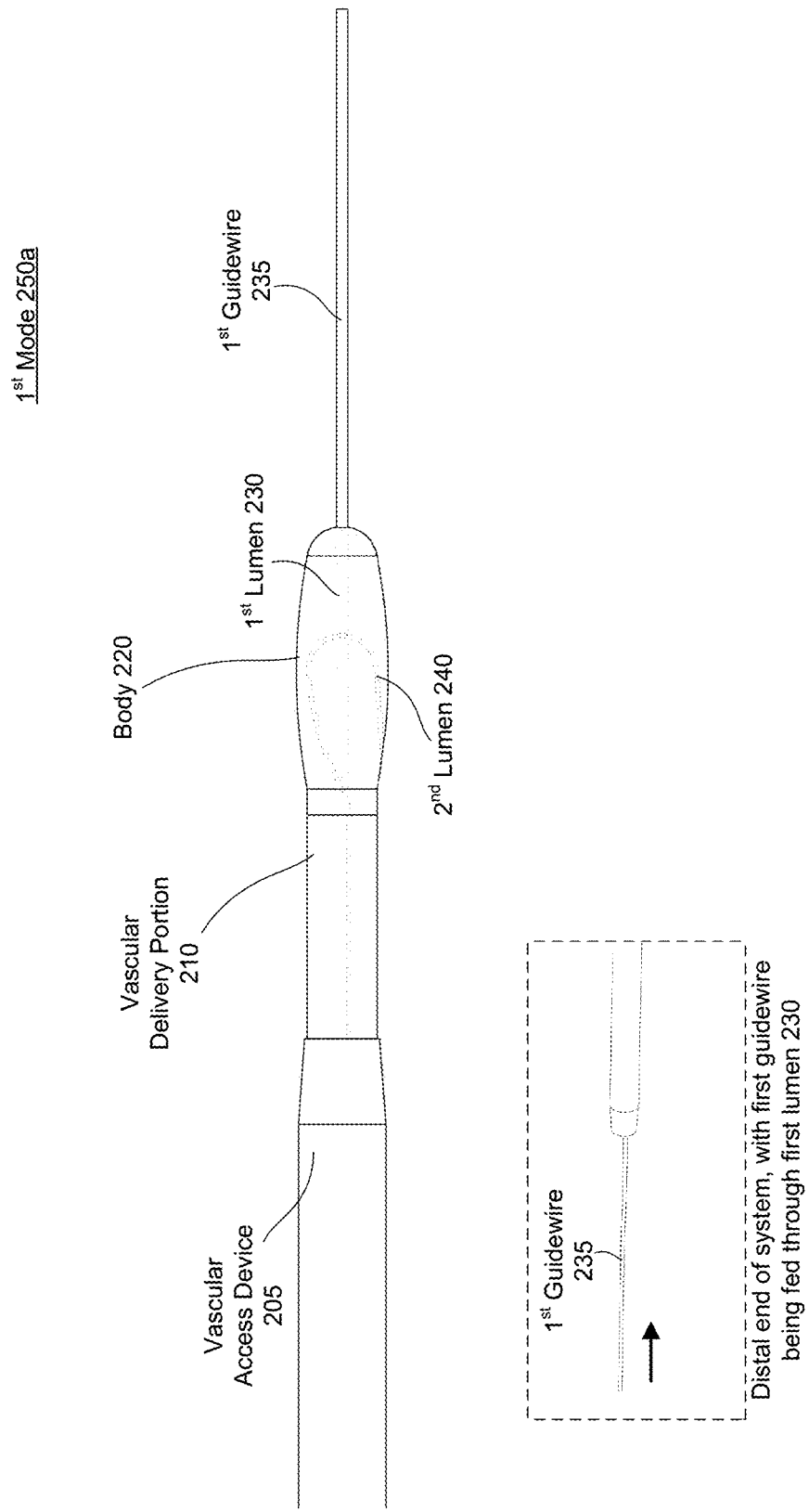
FIG. 2C is a schematic of a second phase of use of the embodiment of the system shown in FIG. 2A.

FIG. 2C is a schematic of a second phase of use of the embodiment of the system shown in FIG. 2A. In FIG. 2C, the system 200 is in the first mode 250a of use, with first guidewire 235 passing through the first lumen 230 in a retrograde direction. The inset schematic in dashed lines depicts a distal end of the system 200, where the first guidewire is being fed through the first lumen 230 in the retrograde direction.

Figure 2D:
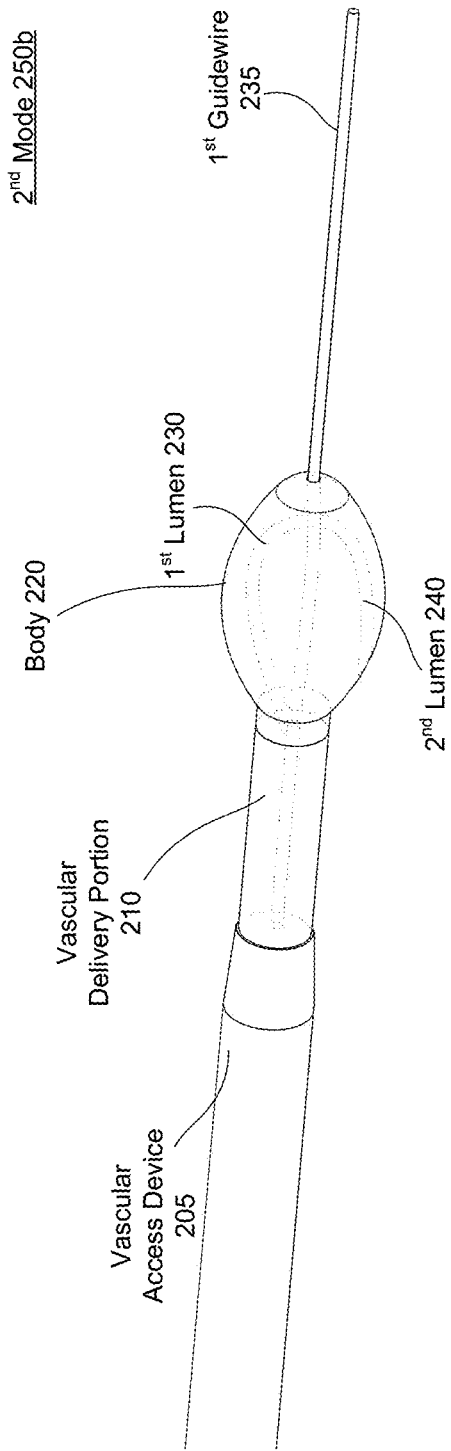
FIG. 2D is a schematic of a third phase of use of the embodiment of the system shown in FIG. 2A.

FIG. 2D is a schematic of a third phase of use of the embodiment of the system shown in FIG. 2A. In FIG. 2D, the system 200 is transitioning from the first mode 250a to a second mode 250b for transmission of a guidewire (e.g., a second guidewire) in an antegrade direction within the target vessel. In FIG. 2D the body 220 is in an expanded mode with the first guidewire 235 still passing through the first lumen 230, so as to block access by another guidewire. In the second mode 250b, the body 220 is expanded, thereby adjusting a shape of the second lumen 240, such that a guidewire (e.g., second guidewire) can pass through the second lumen 240 in an antegrade direction. As described above, the body 220 shown in FIG. 2D is expanded by pressurization (by liquid, gas, or another fluid) of an interior portion of the body 220 through an opening with a valve (not shown in FIG. 2D).

Figure 2E:
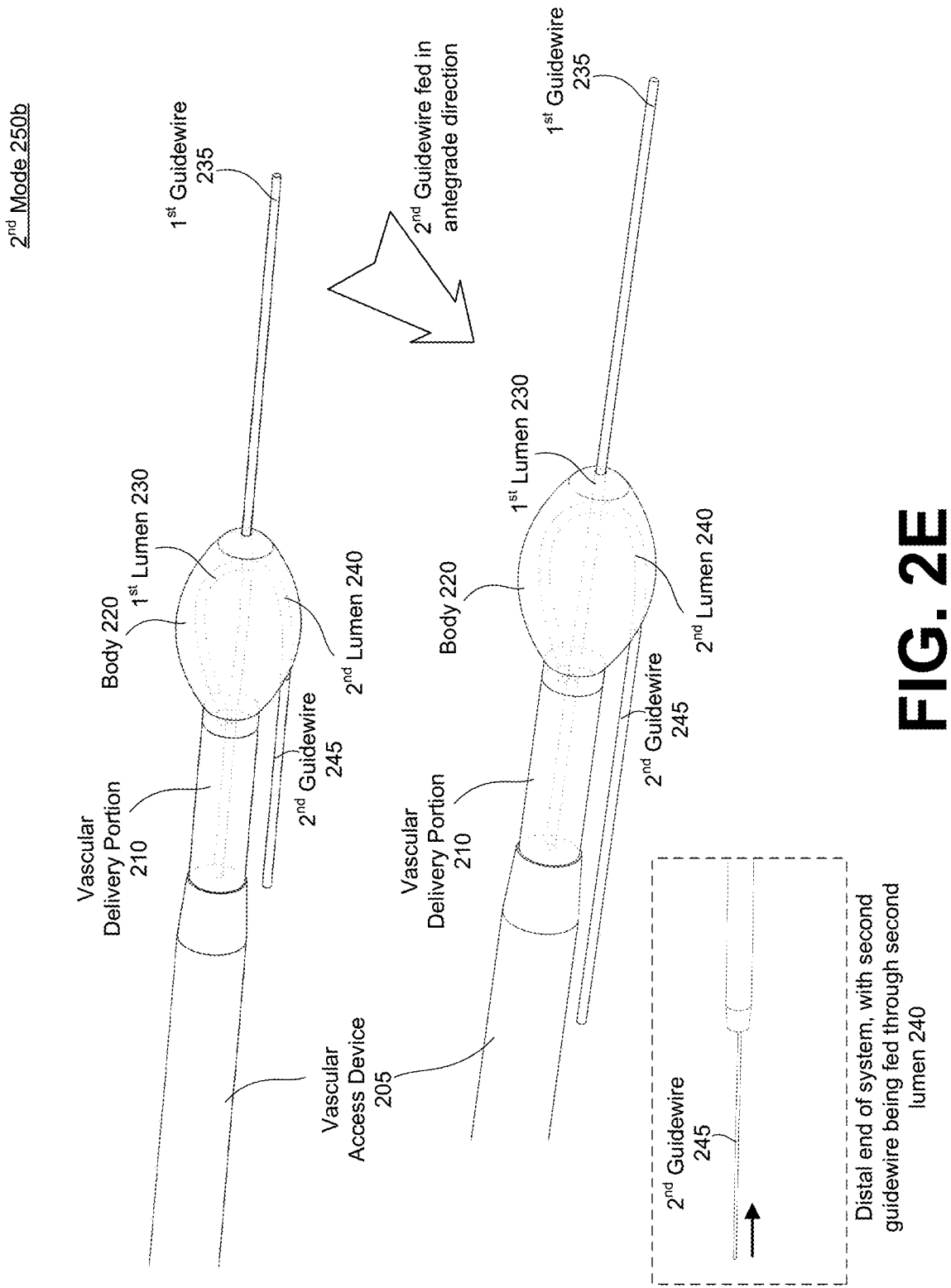
FIG. 2E is a schematic of a fourth phase of use of the embodiment of the system shown in FIG. 2A.

FIG. 2E is a schematic of a fourth phase of use of the embodiment of the system shown in FIG. 2A. In FIG. 2E, the system 200 is in the second mode 250b, with the body 220 expanded and with the first guidewire 235 still passing through the first lumen 230. The second guidewire 245 is being fed through second lumen 240 in the antegrade direction. The second mode 250b thus allows a guidewire to be routed in an antegrade direction through the target vessel, after attempts at retrograde delivery have been made, and without generation of another access site (e.g., near the initial access site or at a contralateral position).

Figure 2F:
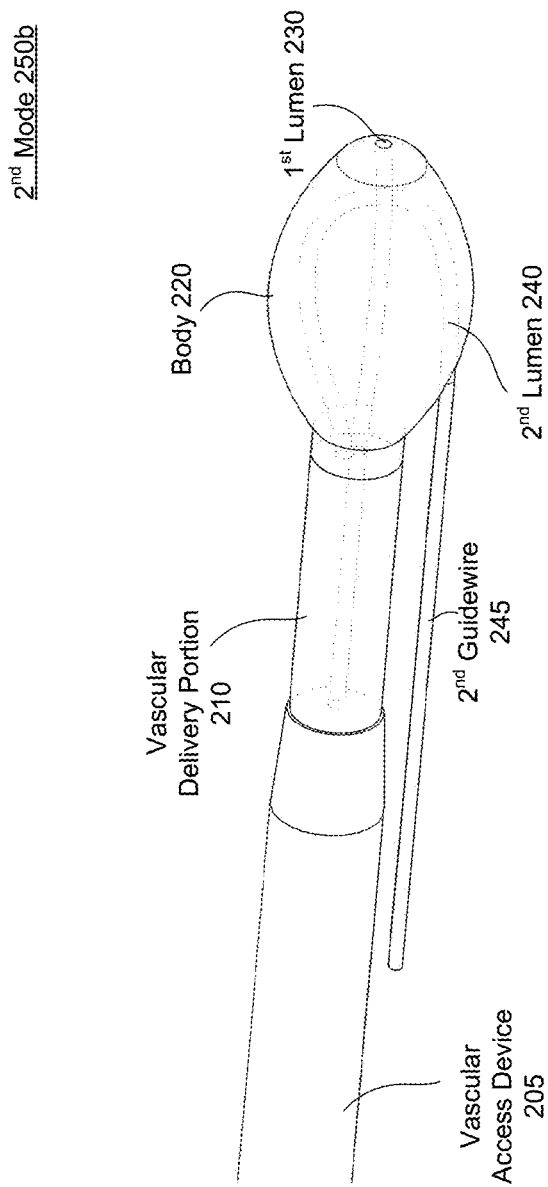
FIG. 2F is a schematic of a fifth phase of use of the embodiment of the system shown in FIG. 2A.

FIG. 2F is a schematic of a fifth phase of use of the embodiment of the system shown in FIG. 2A. In FIG. 2F, the system 200 is in the second mode 250b, with the first guidewire removed from the first lumen 230, while the second guidewire 245 is passing through second lumen 240 in the antegrade direction.

Figure 2G:
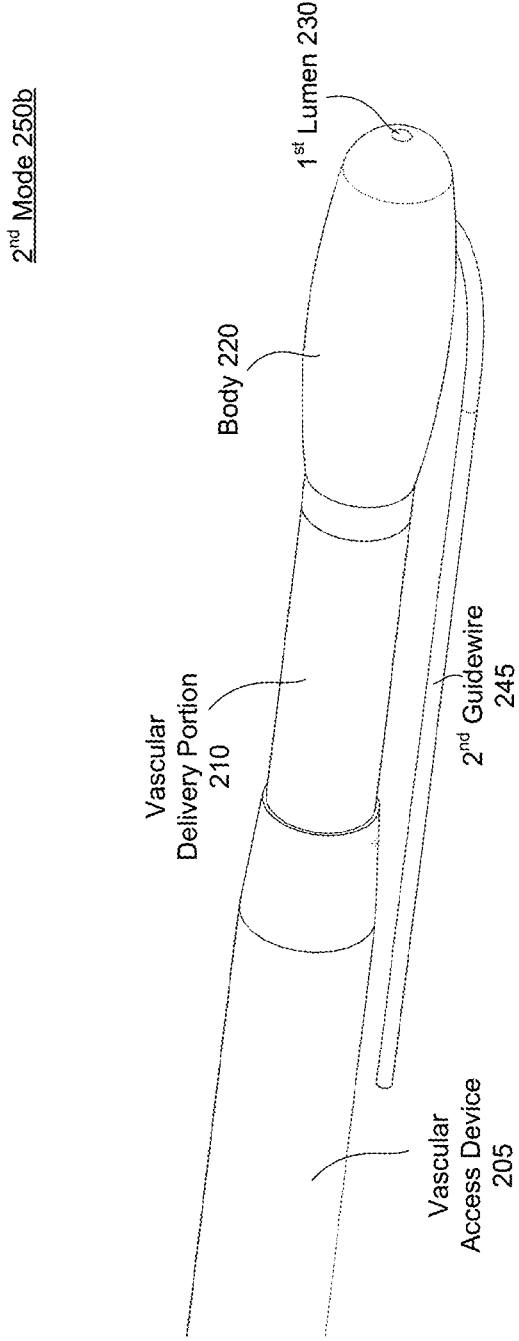
FIG. 2G is a schematic of a sixth phase of use of the embodiment of the system shown in FIG. 2A.

FIG. 2G is a schematic of a sixth phase of use of the embodiment of the system shown in FIG. 2A. In FIG. 2G, the system 200 is transitioning from the second mode 250b, with expansion of the body 220 reversed, while the second guidewire 245 is passing through second lumen 240 in the antegrade direction. As described above, the body 220 shown in FIG. 2G is deflated by depressurization (of liquid, gas, or another fluid) of an interior portion of the body 220 through an opening with a valve (not shown in FIG. 2G).

Figure 2H:
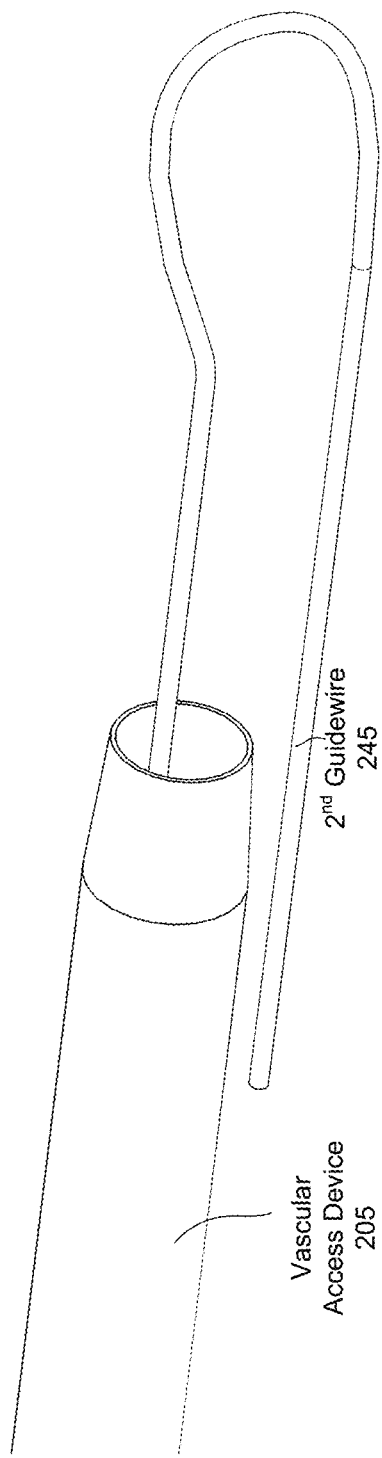
FIG. 2H is a schematic of a seventh phase of use of the embodiment of the system shown in FIG. 2A.

FIG. 2H is a schematic of a seventh phase of use of the embodiment of the system shown in FIG. 2A. In FIG. 2H, the vascular delivery portion 210 and the body 220 have been removed from the target vessel, through the vascular access device 205, while the second guidewire 245 is passing through the target vessel in the antegrade direction. Deflation of the body 220 thus allows the body 220 and vascular delivery portion 210 to be removed, and enables a guidewire to be routed in an antegrade direction through the target vessel, after attempts at retrograde delivery have been made, and without generation of another access site (e.g., near the initial access site or at a contralateral position).

1.5 System—Other Variations

In an alternative embodiment, the system includes a body configured as a balloon at a distal end of the vascular delivery portion, where the vascular delivery portion is configured as an introducer (as opposed to dilator embodiments described above). The system allows the introducer to deform to the antegrade direction once the balloon is inflated. In operation, the body can be expanded to have a diameter larger than the diameter of the incision/opening into the target vessel. This configuration thus prevents the system from slipping to an undesired configuration during rotation of the vascular delivery portion (e.g., introducer) to the position for antegrade delivery, where the guidewire for antegrade routing can be fed straight on but still through a second lumen and still while a guidewire for retrograde delivery is retained by the introducer.

2. Method

FIG. 3 is a block diagram of a method for vascular access, in accordance with one or more embodiments. The method 300 shown in FIG. 3 includes functionality for allowing access by one or more guidewires, introducers, and/or medical devices (e.g., for introducing contrast agents, surgical instruments, catheters, imaging devices, etc.), to a target vessel in multiple directions, without requiring repeated insertion of a vascular access needle and/or requiring multiple punctures at contralateral peripheral access sites.

As described in relation to the system(s) shown in FIGS. 1-2H above, method 300 includes transitioning a body of a vascular delivery portion of a system between a first mode for preferentially allowing retrograde access through the first lumen to the vessel, and a second mode for preferentially allowing antegrade access through the second lumen to the vessel. In particular, in implementing the method 300, one or more embodiments of the systems 100, 200 described above preferentially provide access, through a first lumen, to a vessel in a retrograde direction in a retrograde delivery mode; and responsive to an applied force, preferentially provide access, through a second lumen, to the vessel in an antegrade direction in an antegrade delivery mode.

In more detail, in FIG. 3, the body, in a baseline state, receives and transmits 310 a first guidewire through a first lumen of the body in a retrograde direction.

The body or other portion of the system then transitions 320 from a first mode to a second mode of operation. As described above, the first mode can be a baseline configuration having a first state of expansion (or deflation), and the second mode can be a configuration having a second state of expansion that allows a second lumen to be accessed by a guidewire for antegrade delivery of the guidewire. In some embodiments, the body may not be expanded or deflated, as described above, and transitioning of the system between retrograde and antegrade delivery modes can be achieved in another manner. In transitioning between the first mode and the second mode, the body (or other portion of the system) can include an opening for coupling to a pumping device, thereby subjecting the interior cavity of the body to a pressure (e.g., positive pressure, negative pressure) that inflates or deflates the body.

As shown in FIG. 3, the body can be configured to transmit a second guidewire (or the first guidewire) into the vessel in an antegrade direction, for instance, if an obstruction is encountered during the first attempt at transmission in the retrograde direction. As such, in FIG. 3, the body can receive and transmit 330 a second guidewire (or the first guidewire) in an antegrade direction through a second lumen of the body. In relation to step 330, the first guidewire can be retained in position in the first lumen, such that the second guidewire can pass into the second lumen without unintentionally accessing the first lumen. The first guidewire can then be removed. Thus, in relation to preferentially providing access to the vessel in the retrograde direction and transitioning to preferentially providing access to the vessel in the antegrade direction, the method 300 can provide a mechanism for providing access to the vessel in a retrograde direction by way of a first puncture site, and transitioning to providing access to the vessel in an antegrade direction by way of the first puncture site, without repeatedly puncturing the first puncture site or generating a second puncture site.

The body can then be transitioned 340 from the second mode (e.g., to a deflated configuration), such that the body can be removed and so that subsequent portions of a procedure can be performed. As described in relation to FIGS. 1-2H above, the body can be deflated or otherwise deformed to allow for easy removal (e.g., from the vessel, from the vascular access needle).

Finally, the body is removed 250 (e.g., through a vascular access device, etc.), such that the system provides an antegrade delivery mode without requiring repeated insertion of a vascular access device (e.g., needle) and/or requiring multiple punctures at contralateral peripheral access sites.

3. Conclusion

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method for vascular access, the method comprising:
   preferentially providing access, through a first lumen, to a vessel in a retrograde direction in a retrograde delivery mode; and
   responsive to an applied force, preferentially providing access, through a second lumen, to the vessel in an antegrade direction in an antegrade delivery mode;
   wherein the applied force is derived from a positive pressure applied within an interior cavity of a body surrounding the first lumen and the second lumen;
   wherein the method further comprising providing an opening, at a surface of the body, for coupling to a pumping device, thereby subjecting the interior cavity to the positive pressure.

2. The method of claim 1, wherein preferentially providing access in the retrograde direction comprises receiving a first guidewire into the first lumen in the retrograde direction.

3. The method of claim 2, wherein preferentially providing access in the antegrade direction comprises receiving at least one of the first guidewire and a second guidewire into the first lumen in the antegrade direction.

4. The method of claim 1, wherein preferentially providing access to the vessel in the retrograde direction comprises providing access to the vessel by way of a first puncture site, and wherein preferentially providing access to the vessel in the antegrade direction comprises providing access to the vessel by way of the first puncture site.

5. The method of claim 4, further comprising transitioning between the retrograde delivery mode and the antegrade delivery mode, using the first puncture site, upon detection of an obstruction within the vessel in the retrograde direction.

6. The method of claim 5, wherein transitioning between the retrograde delivery mode and the antegrade delivery mode omits generation of a second puncture site and performing a repeat puncturing operation at the first puncture site.

7. The method of claim 4, wherein transitioning between the retrograde delivery mode and the antegrade delivery mode comprises transitioning a body surrounding the first lumen and the second lumen between a baseline configuration and an expanded configuration.

8. The method of claim 7, wherein providing access to the vessel comprises delivering a guidewire into the vessel, the method further comprising transitioning the body to a deflated configuration and removing the body from the vessel, with the guidewire positioned within the vessel.

* * * * *